US011000237B2

(12) United States Patent
Gujral et al.

(10) Patent No.: US 11,000,237 B2
(45) Date of Patent: May 11, 2021

(54) INTELLIGENT WARNING SYSTEM

(71) Applicant: MICROSOFT TECHNOLOGY LICENSING, LLC, Redmond, WA (US)

(72) Inventors: Rupreet Singh Gujral, Hyderabad (IN); Varun Kumar Palavalasa, Hyderabad (IN); Noor Mahdi, Wellington (NZ)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 16/600,417

(22) Filed: Oct. 11, 2019

(65) Prior Publication Data
US 2020/0037964 A1 Feb. 6, 2020

Related U.S. Application Data

(63) Continuation of application No. 16/024,205, filed on Jun. 29, 2018, now Pat. No. 10,492,735.

(60) Provisional application No. 62/663,665, filed on Apr. 27, 2018.

(51) Int. Cl.
*A61B 5/00* (2006.01)
*A61B 5/16* (2006.01)
*A61B 5/024* (2006.01)

(52) U.S. Cl.
CPC ............... *A61B 5/746* (2013.01); *A61B 5/00* (2013.01); *A61B 5/165* (2013.01); *A61B 5/742* (2013.01); *A61B 5/024* (2013.01)

(58) Field of Classification Search
CPC ......... A61B 5/00; A61B 5/0165; A61B 5/486; A61B 5/7175; A61B 5/742; A61B 5/7475; A61B 5/746; A61B 5/1118; A61B 2230/50; A61B 2230/63; A61B 5/165; G02B 27/0093
See application file for complete search history.

(56) References Cited

U.S. PATENT DOCUMENTS

| 10,492,735 B2 * | 12/2019 | Gujral ...................... A61B 5/01 |
| 2012/0116202 A1 * | 5/2012 | Bangera .................. G01S 13/88 600/407 |
| 2014/0278229 A1 * | 9/2014 | Hong ...................... A61B 5/486 702/160 |
| 2016/0081612 A1 * | 3/2016 | Yamamoto ............ A61B 5/1118 600/595 |
| 2017/0340920 A1 * | 11/2017 | Posio ...................... G16H 20/70 |
| 2018/0321700 A1 * | 11/2018 | Kwak ................ G05D 23/1919 |
| 2019/0365332 A1 * | 12/2019 | Fedichev ............... G16H 10/20 |

* cited by examiner

*Primary Examiner* — Van T Trieu
(74) *Attorney, Agent, or Firm* — Newport IP, LLC; Benjamin A. Keim (57) ABSTRACT

Various embodiments described herein relate to an intelligent warning system in a communication service. One embodiment of the present invention analyzes a user's biometric signals and image data of one of the user's in a communication session to determine a distress level. In addition, location data indicating the user's velocity and direction can be used to determine a distress level. If the biometric signals or the image data indicate a distress level that meets or exceeds a threshold level, a notification is automatically sent to a remote user. This can allow a remote user to render assistance to a user in distress, even when the user is unable to communicate one or more conditions.

17 Claims, 8 Drawing Sheets

INTELLIGENT WARNING SYSTEM

CROSS-REFERENCE TO RELATED APPLICATIONS

This application claims the benefit of the earlier filing date under 35 U.S.C. § 120 of U.S. patent application Ser. No. 16/024,205 filed on Jun. 29, 2018 and titled "INTELLIGENT WARNING SYSTEM" which claims the right of priority under 35 U.S.C. § 119(e) of U.S. Provisional Patent Application No. 62/663,665, filed on Apr. 19, 2018 and titled "INTELLIGENT WARNING SYSTEM." The entire disclosures of both applications are expressly incorporated in their entirety by reference herein.

BACKGROUND

Modern electronic devices come with a plethora of sensors and can do amazing things, yet sometimes they cannot do the most useful and most important tasks. In some instances, during a communication session, for example, it is vital to communicate the user's condition. When users are faced with a possible sudden life-threatening condition, they may be unable to convey that condition to the other user(s), and as such, the other user would be none the wiser to appreciate the severity of the situation.

For example, the user may be experiencing shortness of breath, a heart attack, or stroke, thereby making it difficult, or render the user incapable to speak or deliver a message to the other user of the present condition and urgent need for immediate medical assistance. In other instances, the user may be unaware of his/her present condition, as the onset of a life-threatening condition may be sudden, and the user would not have time to deliver a message to the other user in a chatting session.

Despite having a fully capable device that could monitor the user's pulse, and "see" the user through cameras and environmental awareness, a user may have a dire medical condition yet the device would not know and would take no action to help keep the person safe and/or notify the other user in the chat session so they could intervene. Therefore, there is a need for improved communication systems to address these issues. It is with respect to these and other considerations that the disclosure made herein is presented.

SUMMARY

The present invention provides a method for using a biometric signal in a communication system to generate intelligent warning signals. In some embodiments, one or more streams associated with a communication session comprise biometric data of a user participating in the communication session. For example, a server may be in communication with a network, such as the Internet or cellular network, where it can receive the data from an end-user device, such as a phone or a tablet. The techniques disclosed herein provide a system for analyzing at least one aspect of the biometric data. For example, the server might have access to a biometric detection module, which can analyze the biometric signals and determine a user condition or state.

The system can then determine if an aspect of the biometric data meets one or more criteria. For example, the server might access a biometric data table in memory that lists various characteristics of the biometric signal and associates those characteristics with a known user condition or state. One biometric signal might be the user's pulse and a particular reading might indicate a characteristic of the pulse, such as "the pulse is high" or the "pulse is low." In such cases, the server determines that criteria associated with the user's pulse has been met. Once the criteria has been met, a notification may be generated. The notification can be a graphical display, an audio signal or any other indicator, such as a light or tactile interface. In another example, if a user moves in a particular pattern, velocity, or direction that indicates distress, the server may determine that criteria associated with the user has been met. Thus, if a user is moving in a particular direction or velocity that is outside a defined threshold, a notification may be generated.

In response to determining that one or more criteria has been met, the techniques disclosed herein provide a system that can display a notification on a graphical user interface or generate an audio signal to indicate a condition of a user. In some configurations, a computer may display a rendering of information associated with the biometric data. For example, if the user's pulse rate fell into a range associated with the characteristic of meeting the criteria, e.g., critically close to death, the server would cause to use data from the biometric data table which alerts the other users with the specified notification regarding the user's condition. If the user was found to be moving in a pattern that indicated distress, one or more warnings would be generated for remote users.

In some configurations, the biometric data, the location data indicating movement, and other information associated with the user can be used to generate one or more values indicating a distress level. For instance, the biometric data at a particular heart rate and temperature may cause the generation of the first score, movement patterns from the location data may cause the generation of a second score, and image data from a camera detecting facial expressions or bodily movement can cause the generation of a third score. The scores can be combined or otherwise processed using one or more algorithms to determine an accumulative score which can be compared against the threshold. The notifications described herein can be triggered when the accumulative score meets or exceeds the threshold. It can be appreciated that any of these scores can be used individually or in any combination to determine an accumulative score. Thus, any of the sensors described herein can be used individually or in any combination to generate the notifications described herein.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s), computer-readable instructions, module(s), algorithms, hardware logic, and/or operation(s) as permitted by the context described above and throughout the document.

DETAILED DESCRIPTION

The present invention enables a user's device, such as a cellular phone or smartwatch, to alert another user when the user's physical condition meets a threshold. Computing systems enabled with sensors, capable of measuring at least a pulse and/or movement of a user, and/or equipped with a camera allow for enhanced analysis of the user's physical characteristics to determine a level of distress. In response to determining that the level of distress, a score of which may be compared against a threshold of one or more criteria, one or more notifications may be generated and communicated to remote users. The notifications may simply provide notice of a particular condition or level of distress, or the notifications may provide more detailed descriptions of the user's physical condition or a level of distress.

In one example, the computing device might be a smartphone with a front-facing camera or a wearable device such as a smart-watch. If a user were in a communication session with another user's computing device and began walking or jogging, the system could monitor the velocity of the user, determine the heart rate and in conjunction analyze the user's facial characteristics to determine if delivering an S.O.S. notification would be necessary. In another example, the user might experience a sudden onset of a heart attack or other ailment. The user's pulse rate might dip or spike abnormally low or high. The user may also manifest severe physical expressions of discomfort and distress. Then, the system would analyze these physical characteristics along with a determination of whether the biometric data meets the threshold and warrant an S.O.S. alert to the other computing device.

Figure 1:
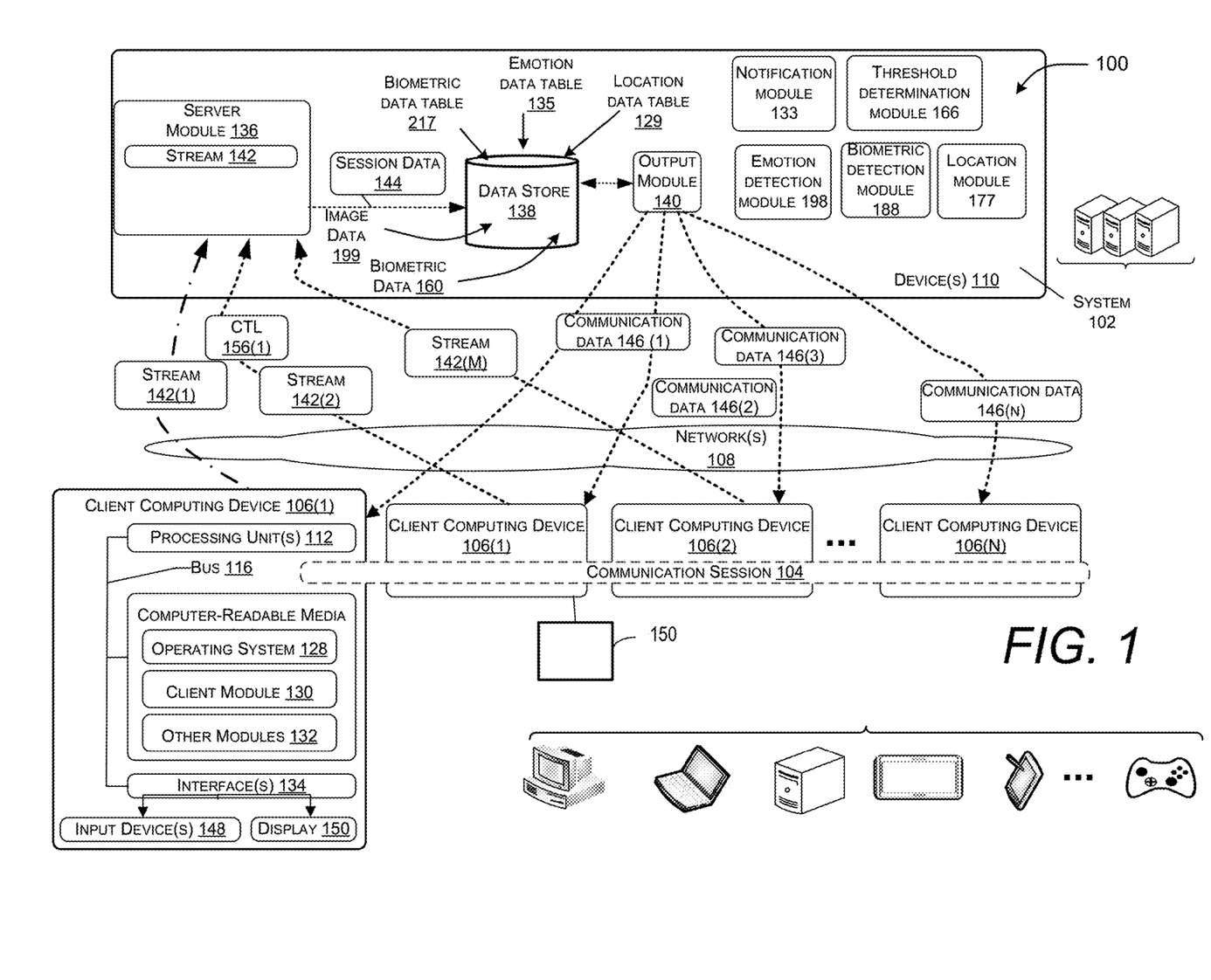
FIG. 1 is a block diagram of a communication system according to an embodiment of the present invention.

The present invention is an intelligent warning system as shown in FIG. 1, which includes a communication session 104 between a number of client computing devices 106(1) through 106(N) (where N is a positive integer number having a value of two or greater). The client computing devices 106(1) through 106(N) enable users to participate in the communication session 104.

In this example, the communication session 104 may be hosted, over one or more network(s) 108, by the system 102. That is, the system 102 may provide a service that enables users of the client computing devices 106(1) through 106(N) to participate in the communication session 104. As an alternative, the communication session 104 may be hosted by one of the client computing devices 106(1) through 106(N) utilizing peer-to-peer technologies.

The system 102 includes device(s) 110, and the device(s) 110 and/or other components of the system 102 may include distributed computing resources that communicate with one another, with the system 102, and/or with the client computing devices 106(1) through 106(N) via the one or more network(s) 108. In some examples, the system 102 may be an independent system that is tasked with managing aspects of one or more communication sessions 104.

Network(s) 108 may include, for example, public networks such as the Internet, private networks such as an institutional and/or personal intranet, or some combination of private and public networks. Network(s) 108 may also include any type of wired and/or wireless network, including but not limited to local area networks ("LANs"), wide area networks ("WANs"), satellite networks, cable networks, Wi-Fi networks, WiMax networks, mobile communications networks (e.g., 3G, 4G, and so forth) or any combination thereof. Network(s) 108 may utilize communications protocols, including packet-based and/or datagram-based protocols such as Internet protocol ("IP"), transmission control protocol ("TCP"), user datagram protocol ("UDP"), or other types of protocols. Moreover, network(s) 108 may also include a number of devices that facilitate network communications and/or form a hardware basis for the networks, such as switches, routers, gateways, access points, firewalls, base stations, repeaters, backbone devices, and the like.

In some examples, network(s) 108 may further include devices that enable connection to a wireless network, such as a wireless access point ("WAP"). Example networks support connectivity through WAPs that send and receive data over various electromagnetic frequencies (e.g., radio frequencies), including WAPs that support Institute of Electrical and Electronics Engineers ("IEEE") 802.11 standards (e.g., 802.11g, 802.11n, and so forth), and other standards.

In various examples, device(s) 110 may include one or more computing devices that operate in a cluster or other grouped configuration to share resources, balance load, increase performance, provide fail-over support or redundancy, or for other purposes. For instance, device(s) 110 may belong to a variety of classes of devices such as traditional server-type devices, desktop computer-type devices, and/or mobile-type devices. Thus, although illustrated as a single type of device—a server-type device—device(s) 110 may include a diverse variety of device types and are not limited to a particular type of device. Device(s) 110 may represent, but are not limited to, server computers, desktop computers, web-server computers, personal computers, mobile computers, laptop computers, mobile phones, tablet computers, or any other sort of computing device.

A client computing device (e.g., one of client computing device(s) 106(1) through 106(N)) may belong to a variety of classes of devices, which may be the same as, or different from, device(s) 110, such as traditional client-type devices, desktop computer-type devices, mobile-type devices, special purpose-type devices, embedded-type devices, and/or wearable-type devices. Thus, a client computing device can include, but is not limited to, a desktop computer, a game console and/or a gaming device, a tablet computer, a personal data assistant ("PDA"), a mobile phone/tablet hybrid, a laptop computer, a communication device, a computer navigation type client computing device such as a satellite-based navigation system including a global positioning system ("GPS") device, a wearable device, a virtual reality ("VR") device, an augmented reality (AR) device, an implanted computing device, an automotive computer, a network-enabled television, a thin client, a terminal, an Internet of Things ("IoT") device, a work station, a media player, a personal video recorder ("PVR"), a set-top box, a camera, an integrated component (e.g., a peripheral device) for inclusion in a computing device, an appliance, or any other sort of computing device. In some implementations, a client computing device includes input/output ("I/O") interfaces that enable communications with input/output devices such as user input devices including peripheral input devices (e.g., a game controller, a keyboard, a mouse, a pen, a voice input device, a touch input device, a gestural input device, and the like) and/or output devices including peripheral output devices (e.g., a display, a printer, audio speakers, a haptic output device, and the like).

Client computing device(s) 106(1) through 106(N) of the various classes and device types can represent any type of computing device having one or more processing unit(s) 112 operably connected to computer-readable media 114 such as via a bus 116, which in some instances can include one or more of a system bus, a data bus, an address bus, a PCI bus, a Mini-PCI bus, and any variety of local, peripheral, and/or independent buses. The computer-readable media 114 may store executable instructions and data used by programmed functions during operation. Examples of functions implemented by executable instructions stored on the computer-readable media 114 may include, for example, an operating system 128, a client module 130, other modules 132, and programs or applications that are loadable and executable by processing unit(s) 112.

Client computing device(s) 106(1) through 106(N) may also include one or more interface(s) 134 to enable communications with other input devices 148 such as network interfaces, cameras, keyboards, touch screens, and pointing devices (mouse). For example, the interface(s) 134 enable communications between client computing device(s) 106(1) through 106(N) and other networked devices, such as device(s) 110 and/or devices of the system 102, over network(s) 108. Such network interface(s) 134 may include one or more network interface controllers (NICs) or other types of transceiver devices to send and receive communications and/or data over a network.

In the example environment 100 of FIG. 1, client computing devices 106(1) through 106(N) may use their respective client modules 130 to connect with one another and/or other external device(s) in order to participate in the communication session 104. For instance, a first user may utilize a client computing device 106(1) to communicate with a second user of another client computing device 106(2). When executing client modules 130, the users may share data, which may cause the client computing device 106(1) to connect to the system 102 with the other client computing devices 106(2) through 106(N) over the network(s) 108.

The client module 130 of each client computing device 106(1) through 106(N) may include logic that detects user input and communicates control signals to the server relating to controlling aspects of the communication session 104. For example, the client module 130 in the first client computing device 106(1) in FIG. 1 may detect a user input at an input device 148. The user input may be sensed, for example, as a finger press on a user interface element displayed on a touchscreen, or as a click of a mouse on a user interface element selected by a pointer on the display 150. The client module 130 translates the user input according to a function associated with the selected user interface element.

As discussed above, one or more streams from client computing devices 106 in environment 100 comprise image data 199 of a user participating in the communication session 104. The client module 130 may send a control signal 156(1) (also referred to herein as a "control command" or an "indication") to a server (for example, a server operating on the device 110) to perform the desired function.

In one embodiment, the system 102 may receive one or more streams associated with a communication session 104, the one or more streams comprising image data 199 of a user participating in the communication session 104. The system 102 may analyze the image data by examining at least one physical feature of the user using an emotion detection module 198 to determine an emotion signal. If an emotion is detected, it selects the emotion signal from a list of emotions in an emotion data table 135.

For example, a first user in a communication session 104 may be experiencing sudden, sharp pains in her body. At this time, her expression may change from a neutral one to a grimacing, stressed expression. The user's change in expression would be captured and analyzed by the system 102. Next, the user's grimace of pain and stress would be determined to be a change of emotion, and thereby generate an emotion signal. The system 102 would select from a list of emotions in the emotion data table 135.

The system 102 may also use a location module 177. The location module 177 determines the location of the user by receiving location data 111, for example from the GPS sensors of a cellular phone, which are components of one of the client devices 106(1-N), the location module 177 can also track whether the user changes direction by keeping track of the user's motion and location and how many times they change direction. The location module 177 can store this information in a location data table 129. For example, in a health emergency the user could continually move back and forth, which the system 102 detects and can record as a factor in whether the user is physically distressed. The location module 177 tracks the user's movements throughout this time to understand their behavior.

The system 102 also employs a biometric detection module 188 in order to determine a biometric signal. While the user is experiencing sudden and sharp pains through her body, her pulse rate may elevate at a rapid rate. The biometric detection module 188 detects the elevated pulse rate and keeps track of the pulse values.

The system 102 also includes a threshold determination module 166 (TDM 166). The TDM 166 accesses the data store 138 to retrieve values from the location data table 129, the biometric data table 217, and the emotion data table 135 and applies these values to a formula to determine if a threshold has been met or exceeded. If the threshold is exceeded the TDM 166 sends a signal to the notification module 133.

At the instance the TDM 166 has informed the notification module 133, it sends a notification 218 to the other user's client computing devices 106 (1-N) participating in the communication session 104. In this example, the TDM 166 has received all three signals from the user while she has experienced these sudden and sharp pains throughout her body and if it is determined that the user has met the threshold, the system would send a notification 218 to the other users participating in the communication session that the user was in distress, in need of assistance, and would share the user's location.

As shown in FIG. 1, the device(s) 110 of the system 102 includes a server module 136, a data store 138, and an output module 140. The server module 136 is configured to receive, from individual client computing devices 106(1) through 106(N), streams 142(1) through 142(M) (where M is a positive integer number equal to 2 or greater). In some scenarios, not all the client computing devices utilized to participate in the communication session 104 provide an instance of streams 142, and thus, M (the number of instances submitted) may not be equal to N (the number of client computing devices). In some other scenarios, one or more of the client computing devices 106 may be communicating an additional stream 142 that includes content, such as a document or other similar type of media intended to be shared during the communication session 104.

The server module 136 is also configured to receive, generate and communicate session data 144 and to store the session data 144 in the data store 138. The session data 144 can define aspects of a communication session 104, such as the identities of the participants, the content that is shared, etc. In various examples, the server module 136 may select aspects of the streams 142 that are to be shared with the client computing devices 106(1) through 106(N). The server module 136 may combine the streams 142 to generate communication data 146 defining aspects of the communication session 104. The communication data 146 can comprise individual streams containing select streams 142. The communication data 146 can define aspects of the communication session 104, such as a user interface arrangement of the user interfaces on the client computing devices 106, the type of data that is displayed and other functions of the server module 136 and client computing devices. The server module 136 may configure the communication data 146 for the individual client computing devices 106(1)-106(N). Communication data can be divided into individual instances referenced as 146(1)-146(N). The output module 140 may communicate the communication data instances 146(1)-146(N) to the client computing devices 106(1) through 106(N). Specifically, in this example, the output module 140 communicates communication data instance 146(1) to client computing device 106(1), communication data instance 146(2) to client computing device 106(2), communication data instance 146(3) to client computing device 106(3), and communication data instance 146(N) to client computing device 106(N), respectively.

The communication data instances 146(1)-146(N) may communicate audio that may include video representative of the contribution of each participant in the communication session 104. Each communication data instance 146(1)-146(N) may also be configured in a manner that is unique to the needs of each participant user of the client computing devices 106(1) through 106(N). Each client computing device 106(1) through 106(N) may be associated with a communication session view. Examples of the use of communication session views to control the views for each user at the client computing devices 106 are described with reference to FIG. 2.

Figure 2:
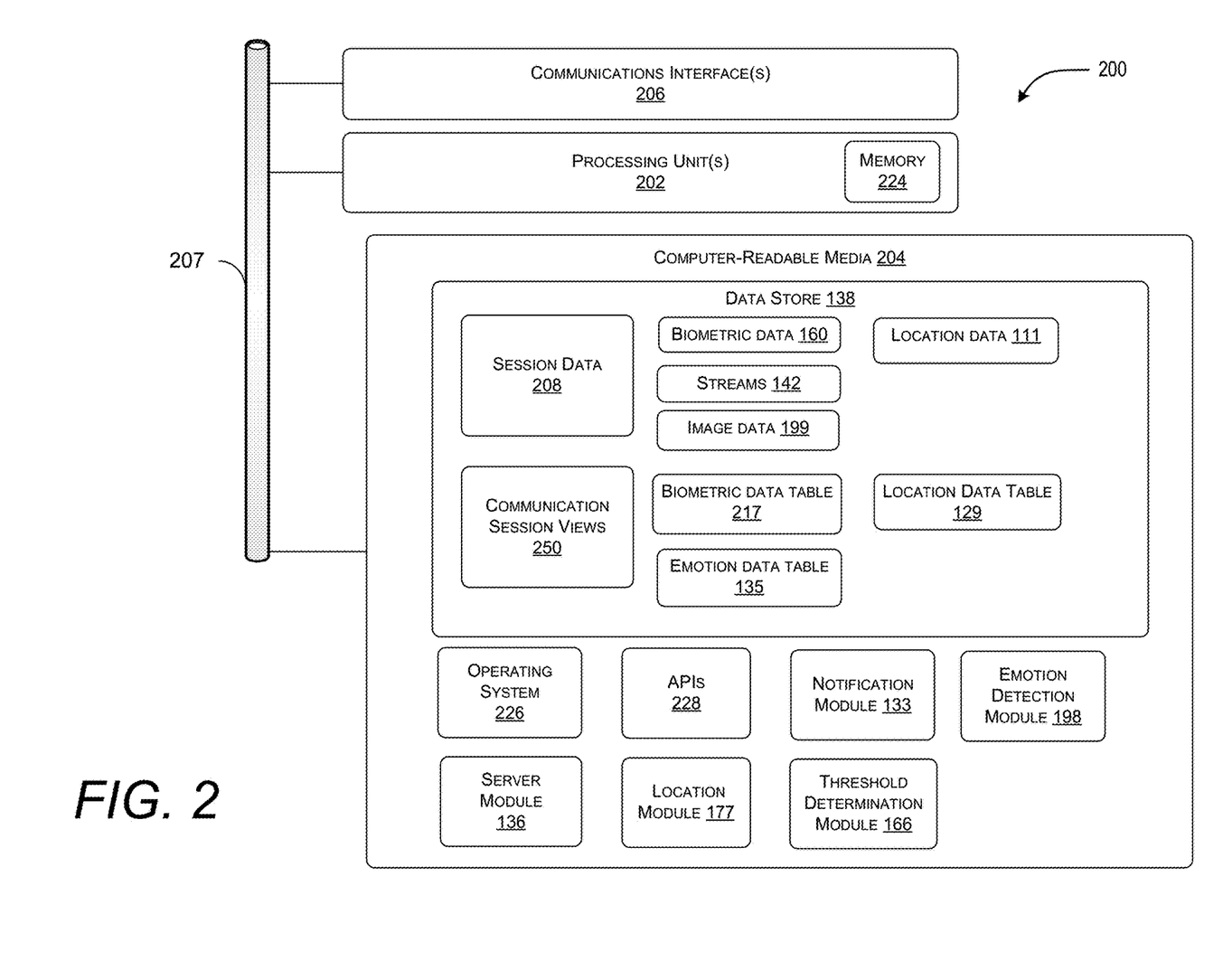
FIG. 2 is a block diagram of an example device in the communication system of FIG. 1.

FIG. 2 is a block diagram of an example device in the communication system of FIG. 1. The device 200 may represent one of device(s) 110 where the device 200 includes one or more processing unit(s) 202, computer-readable media 204, and communication interface(s) 206. The components of the device 200 are operatively connected, for example, via a bus 207, which may include one or more of a system bus, a data bus, an address bus, a PCI bus, a Mini-PCI bus, and any variety of local, peripheral, and/or independent buses.

As utilized herein, processing unit(s), such as the processing unit(s) 202 and/or processing unit(s) 112, may represent, for example, a CPU-type processing unit, a GPU-type processing unit, a field-programmable gate array ("FPGA"), another class of digital signal processor ("DSP"), or other hardware logic components that may, in some instances, be driven by a CPU. For example, and without limitation, illustrative types of hardware logic components that may be utilized include Application-Specific Integrated Circuits ("ASICs"), Application-Specific Standard Products ("ASSPs"), System-on-a-Chip Systems ("SOCs"), Complex Programmable Logic Devices ("CPLDs"), etc.

As utilized herein, computer-readable media, such as computer-readable media 204 and/or computer-readable media 114, may store instructions executable by the processing unit(s). The computer-readable media may also store instructions executable by external processing units such as by an external CPU, an external GPU, and/or executable by an external accelerator, such as an FPGA type accelerator, a DSP type accelerator, or any other internal or external accelerator. In various examples, at least one CPU, GPU, and/or accelerator is incorporated in a computing device, while in some examples one or more of a CPU, GPU, and/or accelerator is external to a computing device.

Computer-readable media may include computer storage media and/or communication media. Computer storage media may include one or more of volatile memory, non-volatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including but not limited to random-access memory ("RAM"), static random-access memory ("SRAM"), dynamic random-access memory ("DRAM"), phase change memory ("PCM"), read-only memory ("ROM"), erasable programmable read-only memory ("EPROM"), electrically erasable programmable read-only memory ("EEPROM"), flash memory, compact disc read-only memory ("CD-ROM"), digital versatile disks ("DVDs"), optical cards or other optical storage media, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In contrast to computer storage media, communication media may embody computer-readable instructions, data structures, program modules, or other data in a modulated data signal, such as a carrier wave, or other transmission mechanism. As defined herein, computer storage media does not include communications media. That is, computer storage media does not include communications media consisting solely of a modulated data signal, a carrier wave, or a propagated signal, per se.

Communication interface(s) 206 may represent, for example, network interface controllers ("NICs") or other types of transceiver devices to send and receive communications over a network. The communication interfaces 206 are used to facilitate communication over a data network with client computing devices 106.

In the illustrated example, computer-readable media 204 includes the data store 138. In some examples, the data store 138 includes data storage such as a database, data warehouse, or other type of structured or unstructured data storage. In some examples, the data store 138 includes a corpus and/or a relational database with one or more tables, indices, stored procedures, and so forth to enable data access including one or more of hypertext markup language ("HTML") tables, resource description framework ("RDF") tables, web ontology language ("OWL") tables, and/or extensible markup language ("XML") tables, for example.

The data store 138 may store data for the operations of processes, applications, components, and/or modules stored in computer-readable media 204 and/or executed by processing unit(s) 202 and/or accelerator(s). For instance, in some examples, the data store 138 may store session data 208 (e.g., session data 144), profile data, and/or other data. The session data 208 may include a total number of participants in the communication session 104, and activity that occurs in the communication session 104 (e.g., behavior, activity of the participants), and/or other data related to when and how the communication session 104 is conducted or hosted. Examples of profile data include, but are not limited to, a participant identity ("ID") and other data.

In an example implementation, the data store 138 stores biometric data 160, image data 199, location data 111 that is received by one or more biometric sensors. The system 102 generates communication data 146 that when displayed by the display of client computing device 106(2), allows the client computing device 106(2) to display any one of the notifications 218 that are associated with the biometric data 160 of the first user, where the biometric data 160 is analyzed from the first user that is in communication with the client computing device 106(1), thereby displaying the notification 218 on the client computing device 106(2) of the second user.

In another example, if the first user's biometric data 160 has a signature that the biometric detection module 188 matches to a physical state of the first user, the view of the second user's display would be changed. For example, if the first and second users are in a communication session 104 and the first user's pulse rate reached a certain value to indicate a high pulse, the notification module 133 selects a notification 218 from a biometric data table 217 that is associated with the physical state of having a high pulse. This causes a display of a notification 218 associated with the first user's biometric data 160 and sends it to the second user's client computing device 106(1-N). As noted above, the data store 138 may store the streams 142, communication session views 250, session data 208, image data 199, biometric data 160 and a biometric data table 217.

Alternately, some or all of the above-referenced data can be stored on separate memories 224 on board one or more processing unit(s) 202 such as a memory on board a CPU-type processor, a GPU-type processor, an FPGA-type accelerator, a DSP-type accelerator, and/or another accelerator. In this example, the computer-readable media 204 also includes an operating system 226 and an application programming interface(s) 228 configured to expose the functionality and the data of the device(s) 110 (e.g., example device 200) to external devices associated with the client computing devices 106(1) through 106(N). Additionally, the computer-readable media 204 includes one or more modules such as the server module 136 and an output module 140, although the number of illustrated modules is just an example, and the number may vary higher or lower. That is, functionality described herein in association with the illustrated modules may be performed by a fewer number of modules or a larger number of modules on one device or spread across multiple devices.

As such and as described earlier, in general, the system 102 is configured to host the communication session 104 with the plurality of client computing devices 106(1) through 106(N). The system 102 includes one or more processing units 202 and a computer-readable medium 204 having encoded thereon computer-executable instructions to cause the one or more processing units 202 to receive streams 142(1) through 142(M) at the system 102 from a plurality of client computing devices 106(1) through 106 (N), select streams 142 based, at least in part, on the communication session view 250 for each user, and communicate communication data 146 defining the communication session views 250 corresponding to the client computing devices 106(1) through 106(N).

The communication data instances 146(1) through 146(N) are communicated from the system 102 to the plurality of client computing devices 106(1) through 106(N). The communication session views 250(1) through 250(N) cause the plurality of client computing devices 106(1) through 106(N) to display views of the communication session 104 under user control. The computer-executable instructions also cause the one or more processing units 202 to determine that the communication session 104 is to transition to a different communication session view of the communication session 104 based on a user communicated control signal 156.

It is noted that the above description of the hosting of a communication session 104 by the system 102 implements the control of the communication session view in a server function of the device 110. In some implementations, the server function of the device 110 may combine all media portions into the communication data 146 for each client computing device 106 to configure the view to display. The information stored in the communication session view as described above may also be stored in a data store 138 of the client computing device 106. The client computing device 106 may receive a user input and translate the user input as being a view switching control signal that is not transmitted to the server. The control signal may be processed on the client computing device itself to cause the display to switch to the desired view. The client computing device 106 may change the display by re-organizing the portions of the communication data 146 received from the server according to the view selected by the user.

Figure 3:
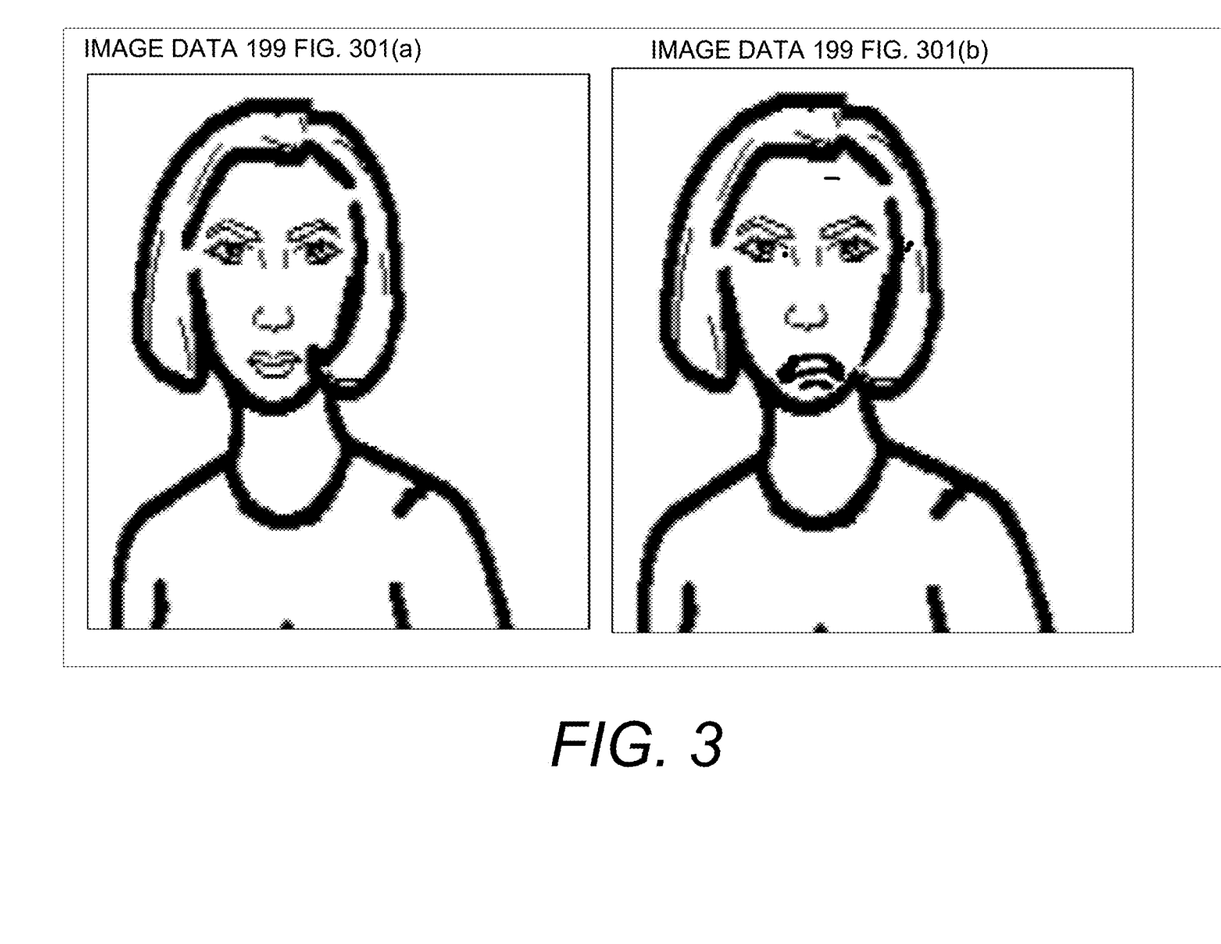
FIG. 3 is an example of image data which is used in communication the system of FIG. 1.

The ability of a user's device to send a notification 218 to other users participating in a communication session 104 is described with reference to screenshots of the display. The user's image may be analyzed to determine an emotion using pattern recognition or other suitable technology. Reference is made to FIG. 3, which illustrates an example of image data 199 that can be analyzed by the system to determine an emotion. The facial expressions can be used to identify an indication of a change in emotion.

For instance, a first user may utilize a client computing device 106(1) to communicate with a second user of another client computing device 106(2). Specifically, FIG. 3 depicts a user participating in a communication session 104. FIG. 3 depicts image data 199 from a client computing device 106(1-N). Image data 199 captured in 301(a) shows the user in a communication session 104 displaying a facial expression that is happy in nature. If during the course of the communication session 104, there was a change in the user's physical condition such that the user's facial expression changed to a sad expression as depicted in 301(b), the emotion detection module 198 can detect the emotion in image data 199 from the user, and in response match it to an emotion in the biometric data table 217 and then send a notification 218 to the other users.

Figure 4A:
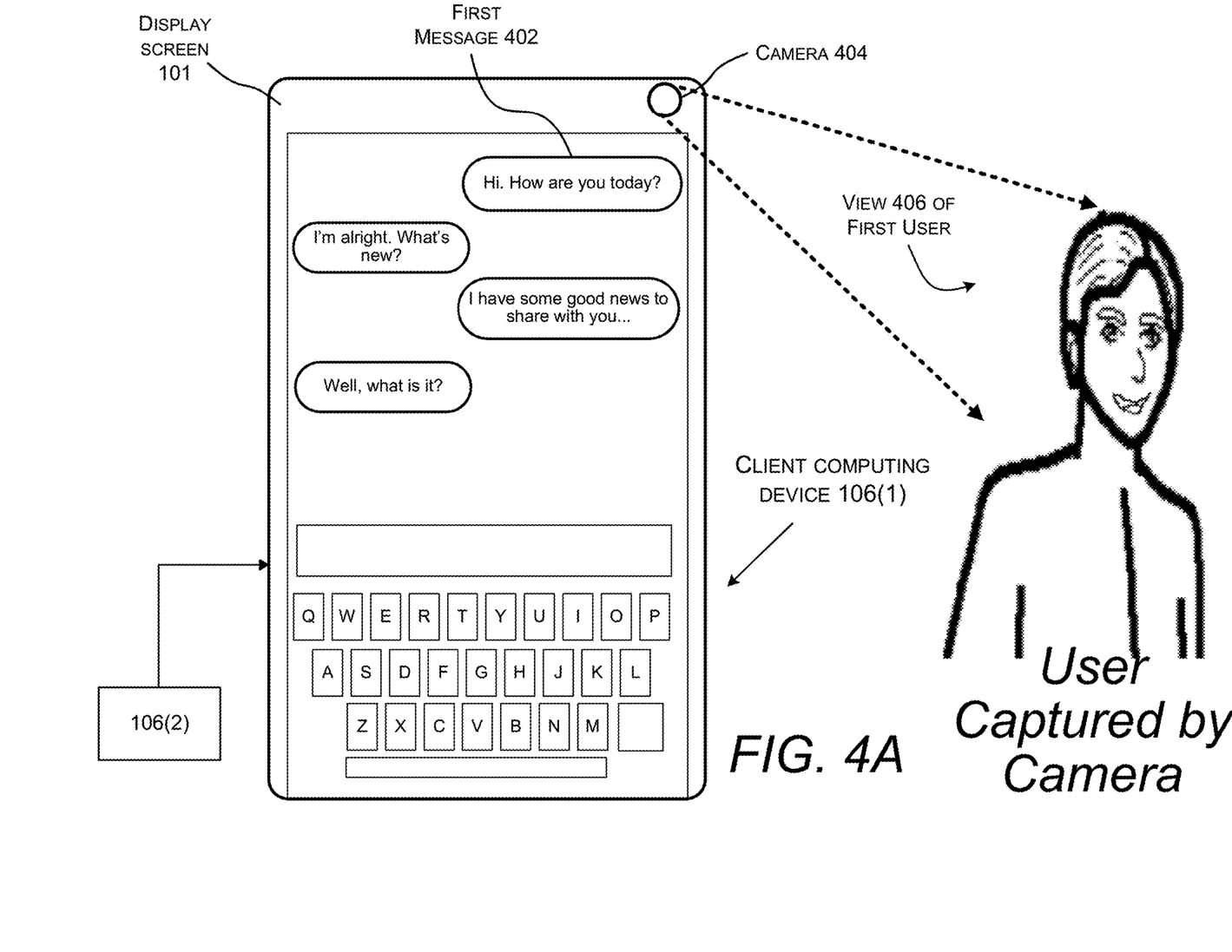
FIG. 4A is a diagram of an example that illustrates an embodiment of the present invention.

Turning now to FIG. 4A, this is a diagram of a communication session 104 between a first user of client computing device 106(1) and a second user of client computing device 106(2) that illustrates an example according to an embodiment of the present invention. This communication session 104 consists of a series of messages that are sent between the client computing devices 106(1) and 106(2). As an example, the first user of client computing device 106(1) has sent a first message 402 to the second user of client computing device 106(2). A camera 404 of the client computing device 106(1) captures a view 406 of the first user during the communication session 104. Note that the camera 404 has captured the view 406 of the first user with a smiling expression which denotes a happy emotion.

Figure 4B:
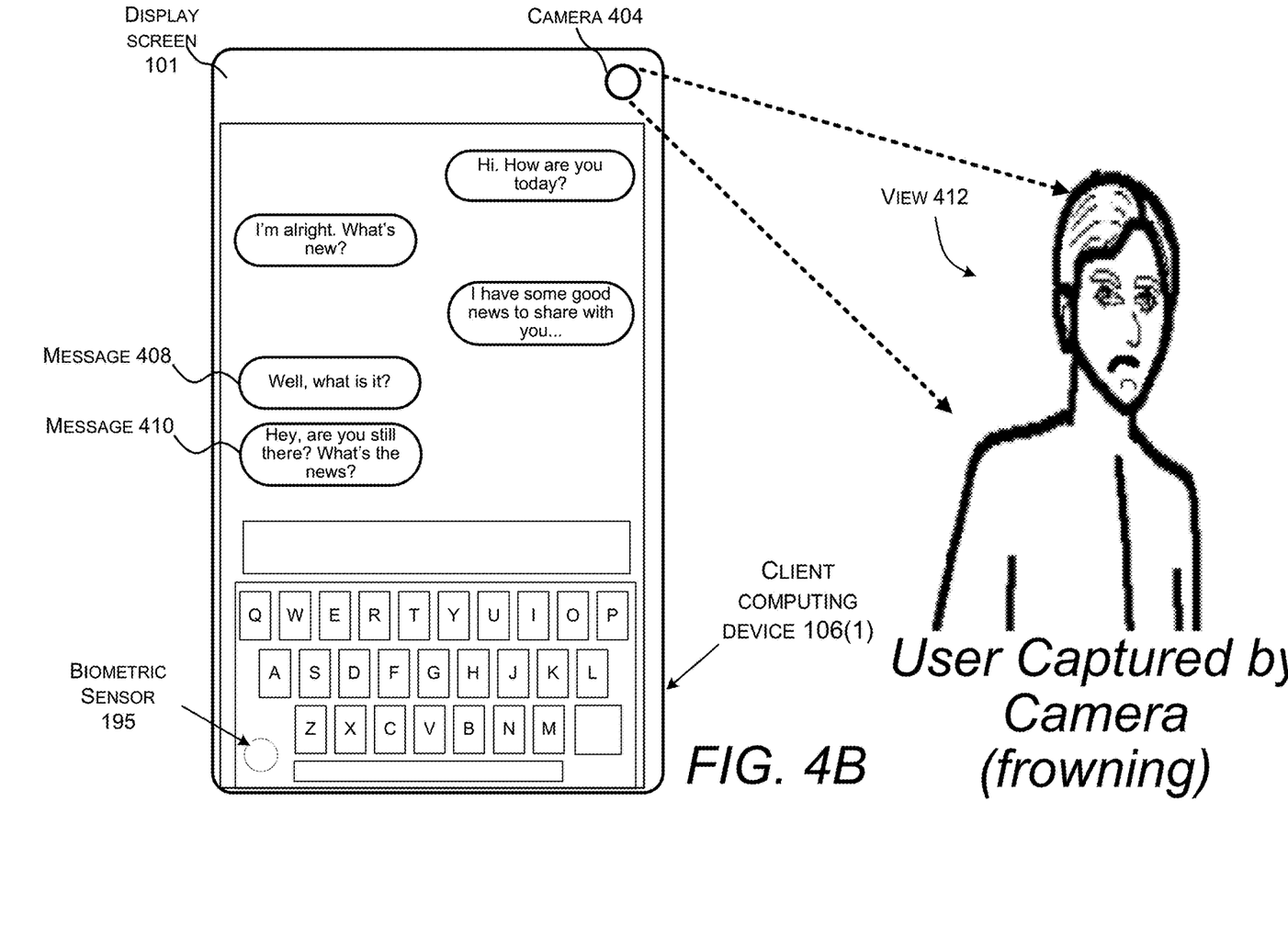
FIG. 4B is a diagram of an example that illustrates an embodiment of the present invention where the image data changes.

Turning now to FIG. 4B, this is a diagram of a continuation of the same communication session 104 as previously described in FIG. 4A. After a series of exchanged messages, the first user has neither responded to the second user's message 408 nor message 410. Also, during this communication session 104, the first user's expression has changed from a smile to a frown as depicted in view 412. As such, the camera 404 of client computing device 106(1) has captured image data 199 of the first user's change in expression.

FIG. 4B also depicts a biometric sensor 195 which would enable a client computing device 106(1-N) to receive biometric values, including but not limited to pulse rate, body temperature, etc. The biometric sensor 195 is intended for illustration purposes only in FIG. 4B. Its location might be an internal component of a wearable computing device such as on a smart watch, or a sensor on a detachable device that connects to the client computing device 106(1-N). In any scenario, the biometric sensor 195 determines the pulse rate of the first user and is continuously operating during the communication session 104 by receiving new values of the user's pulse, for instance.

Figure 4C:
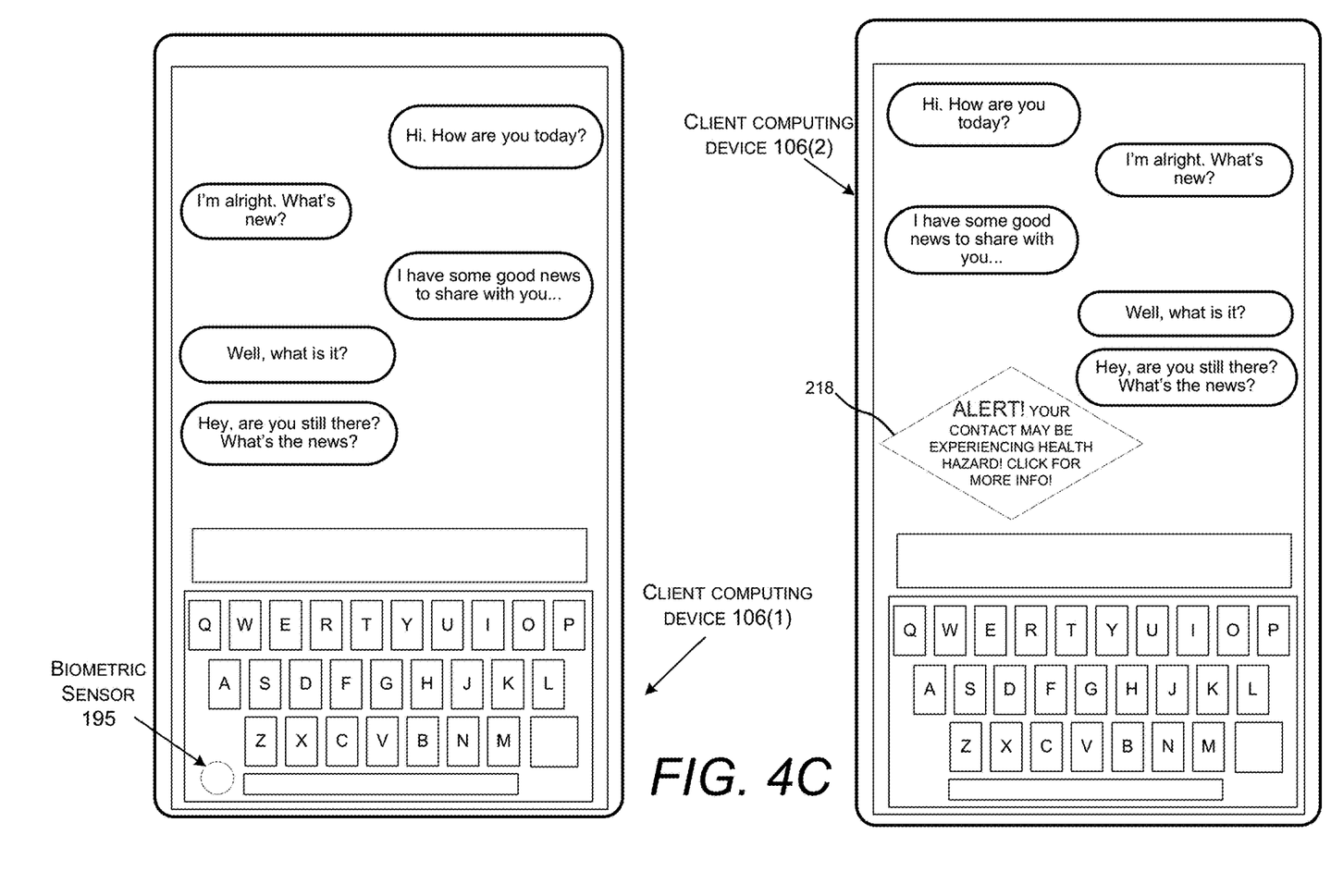
FIG. 4C is a diagram of an example that illustrates an embodiment of the present invention where a notification is sent to another user.

Turning now to FIG. 4C, this is a diagram illustrating a continuation of the communication session 104 of the preceding example. At this time of the communication session 104, the first user of client computing device 106(1) has not responded to the second user's messages 404 or 405. The biometric data 160, image data 199, and location data 111 are used by the TDM 166 to determine whether a serious health condition has arisen which would warrant a notification 218. In this example, the biometric sensor 195 is analyzing this biometric data 160 and determined that the first user's pulse rate has increased dramatically and is unusually high. Also, the image data 199 indicates that the first user's expression has changed from a smile to a frown. Additionally, the location data 111 may have determined that the user's motions are rapid and erratic. It should be understood that location data 111 is continuously monitored and any changes are continuously updated in the system.

As such, in this example, the TDM 166 has made a determination that the first user is experiencing a serious health condition and thus sends a notification 218 to the second user's client computing device 106(2). As illustrated in FIG. 4C, the notification 218 is an alert message which appears on the display screen 101 of the second user's client computing device 106(2). The notification 218 indicates that the first user may have a serious health condition and be in need of assistance.

In other embodiments, different notifications are used. For example, the second user can select the notification 218 in order to obtain specific information about the first user's condition, including but not limited to the specific pulse readings over a period of time, the physical location of the first user, allergy conditions, emergency contacts, blood type, etc.

This allows the second user to understand why the first user has not responded in this instance to previous messages 408 and 410. More importantly, the notification 218 could provide the second user with valuable information to assist the first user in the event of a life-threatening condition. It should be noted, as a consequence of the continuous operation of the TDM 166, if soon after the first user's biometric data 160, image data 199, and location data 111 fell below the threshold, the second user would be notified as such. A notification 218 might alert the other user that the first user's condition has returned to normal levels, for example.

Figure 5:
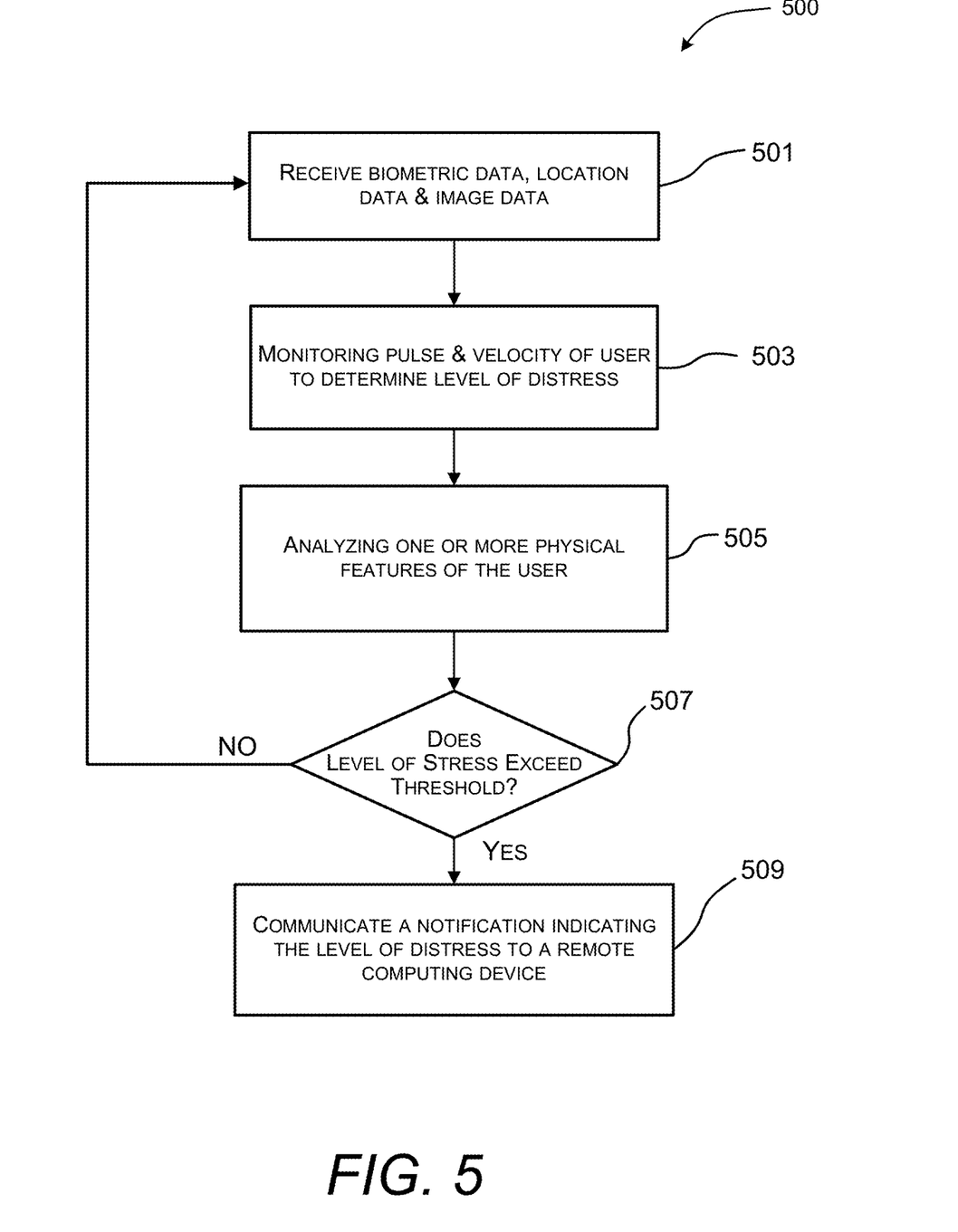
FIG. 5 is a flowchart of an embodiment of the present invention during a communication session.

Turning now to FIG. 5, this is a flowchart illustrating a routine 500 of an operation of a communication session 104 according to an embodiment of the present invention. At step 501 the system receives biometric data 160, location data 111, and image data 199. For example, the user might be using a client computing device such as a cell phone and/or a wearable device such as a smart watch equipped with GPS or other location identifying hardware and a front-facing camera. The client computing device can send information that it receives from all these sensors to the system. The biometric data could be a pulse. The location data could be a specific location where the user is located, and the image data is a picture of the user.

At step 503, the system monitors the pulse and determines the velocity of the user to determine the level of distress. For example, if the user had a wearable device, the device would take the user's pulse and send it to the system 102 and the system 102 would monitor the values it's receiving. In addition, it would receive values linked to the velocity of the user that could be sent from a position sensor or other similar device from the user's client device and sent to the system 102.

At step 505, the system analyzes one or more physical features of the user depicted in the image data, wherein an identification of the one or more physical features influences the level of distress. For example, when the system receives image data, it applies an emotion detection module and compares the images to the results that are associated with distress.

At step 507, the system will determine whether the level of distress exceeds a threshold or not. For example, if the user's pulse is too high, or walking too fast, the threshold could be exceeded. In another example, the user is having an expression of distress or moving too quickly or erratically. Different combinations are possible in different embodiments of the invention to determine if the threshold is met. If the level exceeds a threshold, the system 102 proceeds to step 509 where it communicates a notification 218 indicating the level of distress to a remote computing device. For example, the server sends a notification 218 to another client computing device that is in a communication session with the first user, whereby the second user is notified that the first user is in distress. If the level of distress does not exceed the threshold, no notification 218 is sent and the system will revert back to step 501 receiving biometric data 160, location 111 data, and image data 199.

Figure 6:
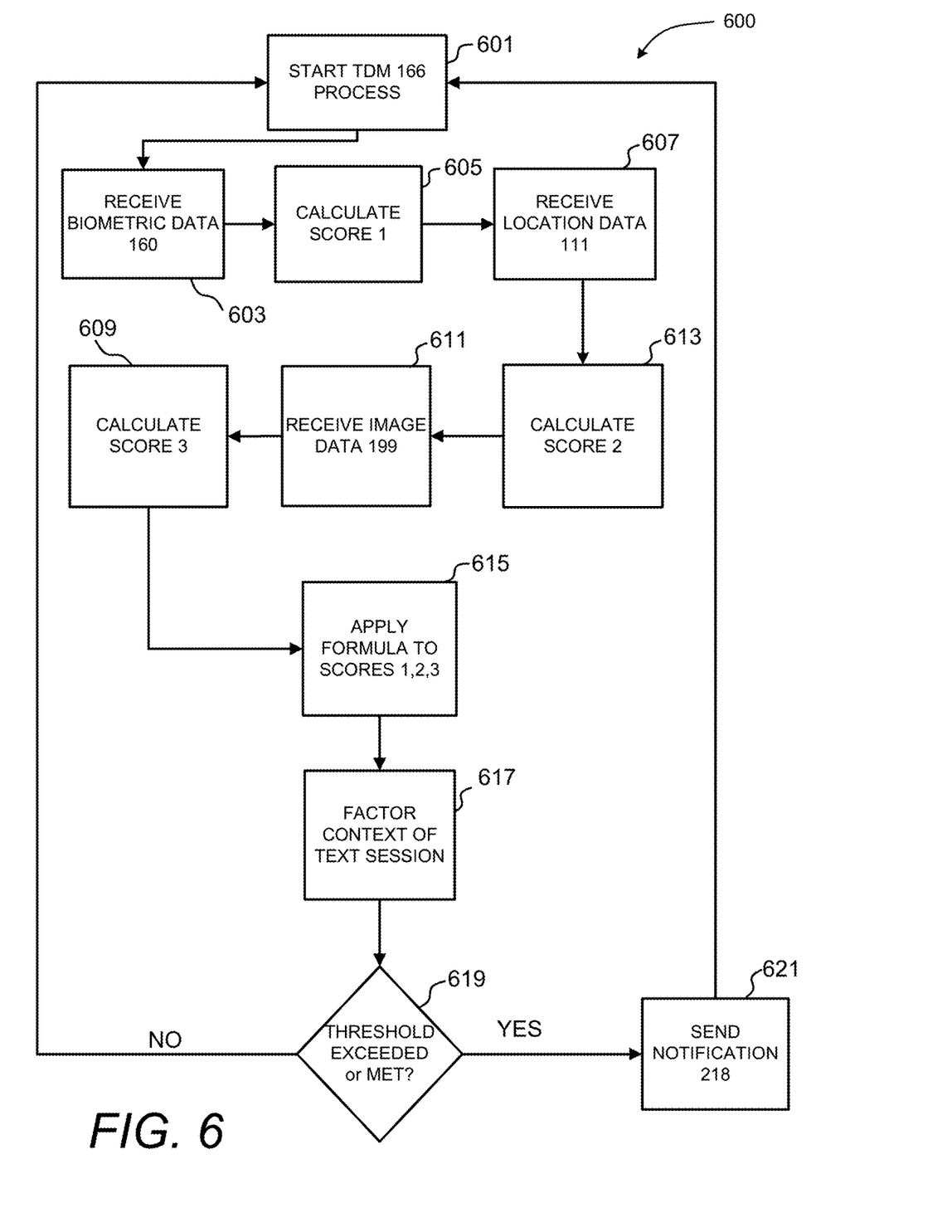
FIG. 6. is a flowchart of an embodiment of the present invention during a communication session.

Turning now to FIG. 6, this is a flowchart illustrating an operation of a communication session 104 according to an embodiment of the present invention. At step 601, the TDM 166 of system 600 begins. Next, at step 603, the system 600 receives biometric data 160 from the biometric sensors. Continuing to step 605, the system 600 calculates the first score of the received biometric data 160. Next, at step 607, the system 600 receives location data 111 and calculates the second score during step 609. Next, at step 611, the system 600 receives image data 199 and calculates the third score during step 613.

At step 615, the system 600 applies a formula to the first score, second score, and third score. Next, at step 617, the system 600 factors the context of the communication session 104. Next, at step 619, the system 600 determines whether a threshold has been exceeded from application of the preceding formula in step 617. If the answer is yes, the system proceeds to step 621 and sends the notification 218 to the client computing device 106(N) of the other user. On the other hand, if the threshold has not been exceeded, the system 600 reverts to step 601 at the start of the TDM 166 process continues.

It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the appended claims.

It also should be understood that the illustrated methods can end at any time and need not be performed in their entireties. Some or all operations of the methods, and/or substantially equivalent operations, can be performed by execution of computer-readable instructions included on a computer-storage media, as defined below. The term "computer-readable instructions," and variants thereof, as used in the description and claims, is used expansively herein to include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

It should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof.

For example, the operations of the routines 500 and/or 600 are described herein as being implemented, at least in part, by an application, component and/or circuit, such as the server module 136 in device 110 in FIG. 1 in the environment 100 hosting the communication session 104. In some configurations, the server module 136 can be a dynamically linked library (DLL), a statically linked library, functionality produced by an application programming interface (API), a compiled program, an interpreted program, a script or any other executable set of instructions. Data and/or modules, such as the server module 136, can be stored in a data structure in one or more memory components. Data can be retrieved from the data structure by addressing links or references to the data structure.

Although the following illustration refers to the components of FIG. 1 and FIG. 2, it can be appreciated that the operations of the routines 500 and/or 600 may also be implemented in many other ways. For example, the routines 500 and/or 600 may be implemented, at least in part, or in modified form, by a processor of another remote computer or a local circuit, such as for example, the client module 130 in the client computing device 106(1). In addition, one or more of the operations of the routines 500 and/or 600 may alternatively or additionally be implemented, at least in part, by a chipset working alone or in conjunction with other software modules. Any service, circuit or application suitable for providing the techniques disclosed herein can be used in operations described herein.

Although the techniques described herein have been described in language specific to structural features and/or methodological acts, it is to be understood that the appended claims are not necessarily limited to the features or acts described. Rather, the features and acts are described as example implementations of such techniques.

The operations of the example processes are illustrated in individual blocks and summarized with reference to those blocks. The processes are illustrated as logical flows of blocks, each block of which can represent one or more operations that can be implemented in hardware, software, or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform functions or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more device(s) such as one or more internal or external CPUs or GPUs, and/or one or more pieces of hardware logic such as FPGAs, DSPs, or other types of accelerators.

All of the methods and processes described above may be embodied in, and fully automated via, software code modules executed by one or more general purpose computers or processors. The code modules may be stored in any type of computer-readable storage medium or other computer storage device. Some or all of the methods may alternatively be embodied in specialized computer hardware.

Conditional language such as, among others, "can," "could," "might" or "may," unless specifically stated otherwise, are understood within the context presented that certain examples include, while other examples do not include, certain features, elements and/or steps. Thus, such conditional language is not generally intended to imply that certain features, elements and/or steps are in any way required for one or more examples, or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

Any routine descriptions, elements or blocks in the flow diagrams described herein and/or depicted in the attached figures should be understood as potentially representing modules, segments, or portions of code that include one or more executable instructions for implementing specific logical functions or elements in the routine. Alternate implementations are included within the scope of the examples described herein in which elements or functions may be deleted, or executed out of order from that shown or discussed, including substantially synchronously or in reverse order, depending on the functionality involved as would be understood by those skilled in the art. It should be emphasized that many variations and modifications may be made to the above-described examples, the elements of which are to be understood as being among other acceptable examples. All such modifications and variations are intended to be included herein within the scope of this disclosure and protected by the following claims.

We claim:

1. A method for identifying a level of distress of a user interacting with a computing device, comprising:
  receiving biometric data indicating at least a pulse of the user, location data indicating a location of the user, and image data depicting a facial expression of the user;
  determining a velocity of the user based on the location data;
  monitoring the pulse of the user and the velocity of the user;
  analyzing the facial expression of the user, wherein an identification of a facial expression feature influences an increase of the level of distress;
  determining the level of distress based on the pulse of the user, the velocity of the user, and the facial expression of the user; and
  in response to determining that the level of distress exceeds a threshold, communicating a notification to a remote computing device, wherein the user of the computing device and a user of the remote computing device are engaged in a communication session prior to the determining that the level of distress exceeds the threshold, and wherein the determining the level of distress is further based on a context of the communication session.

2. The method of claim 1, wherein the level of distress is represented by an accumulative score derived from a first score based on the pulse of the user, a second score based on the velocity of the user, and a third score based on the facial expression of the user.

3. The method of claim 1, wherein an increase in the pulse of the user above an upper predetermined pulse level increases the level of distress or a decrease in the pulse of the user below a lower predetermined pulse level increases the level of distress.

4. The method of claim 3, wherein the upper predetermined pulse level and the lower predetermined pulse level are stored in a biometric data table that lists pulse levels in association with user conditions.

5. The method of claim 1, wherein the biometric data additionally indicates a temperature of the user, wherein a rise in the temperature of the user above an upper threshold temperature increases the level of distress or a decrease in the temperature of the user below a lower threshold temperature increases the level of distress.

6. A computer system for identifying a level of distress of a user, comprising:
  a biometric sensor for receiving biometric data of the user;
  a camera for capturing image data depicting a facial expression of the user;
  a monitoring module to monitor the biometric data and the facial expression;
  one or more processors; and
  a computer storage medium having computer-executable instructions stored thereupon which, when executed by the one or more processors, cause the computing system to:
    receive the biometric data from the biometric sensor, the biometric data indicating at least a pulse of the user;
    receive location data indicating a location of the user;
    receive the image data depicting the physical feature of the user;
    monitor the pulse of the user and the location of the user;
    analyze the facial expression of the user, wherein an identification of a predetermined facial expression influences an increase of the level of distress;
    determine the level of distress based on the pulse of the user, the location of the user, and the facial expression of the user; and
    in response to a determination that the level of distress exceeds a threshold, communicate a notification to a remote computing device, wherein the user of the computer system and a user of the remote computing device are engaged in a communication session prior to the determination that the level of distress exceeds the threshold, and wherein the determination of the level of distress is further based on a context of the communication session.

7. The computer system of claim 6, wherein the level of distress is represented by an accumulative score derived from a first score based on the pulse of the user, a second score based on the location of the user, and a third score based on the facial expression of the user.

8. The computer system of claim 6, further comprising a data store comprising a biometric data table, an emotion data table, and a location data table, wherein the biometric data table lists pulse levels in association with user conditions, the emotion data table lists facial expressions in association with emotions, and the location data table stores a record of the location of the user and a number of times that the user changes direction.

9. The computer system of claim 8, wherein the determination that the level of distress exceeds the threshold is determined by application of a formula to a value retrieved from the biometric data table, a value retrieved from the location data table, and a value retrieved from the emotion data table.

10. The computer system of claim 6, further comprising determining a velocity of the user based on location data, wherein the determination of the level of distress is further based on the velocity of the user.

11. The computer system of claim 6, wherein an increase in the pulse of the user above an upper predetermined pulse level increases the level of distress or a decrease in the pulse of the user below a lower predetermined pulse level increases the level of distress.

12. The computer system of claim 6, wherein the biometric data additionally indicates a temperature of the user, wherein a rise in the temperature of the user above an upper threshold temperature increases the level of distress or a decrease in the temperature of the user below a lower threshold temperature increases the level of distress.

13. A computer storage medium having computer-executable instructions stored thereupon which, when executed by one or more processors of a computing system, cause the computing system to:
  receive, from a computing device, biometric data of a user from a biometric sensor, location data indicating a location of the user, and image data depicting a facial expression of the user;
  monitor the biometric data of the user and the location of the user;
  analyze the facial expression of the user, wherein an identification of a predetermined facial expression influences an increase of a level of distress of the user;

determine the level of distress based on the biometric data of the user, the location of the user, and the facial expression of the user; and in response to a determination that the level of distress exceeds a threshold, communicate a notification to a remote computing device, wherein the user of the computing device and a user of the remote computing device are engaged in a communication session prior to the determination that the level of distress exceeds the threshold, and wherein the determination that the level of distress exceeds the threshold is further based on a context of the communication session.

14. The computer storage medium of claim 13, wherein the level of distress is represented by an accumulative score derived from a first score based on the biometric data of the user, a second score based on the location of the user, and a third score based on the facial expression of the user.

15. The computer storage medium of claim 13, wherein instructions further cause the computing system to determine a velocity of the user based on the location data, wherein the determination that the level of distress exceeds the threshold is further based on the velocity of the user.

16. The computer storage medium of claim 13, wherein the biometric data indicates a temperature of the user, wherein a rise in the temperature of the user above an upper threshold temperature increases the level of distress or a decrease in the temperature of the user below a lower threshold temperature increases the level of distress.

17. The computer storage medium of claim 13, wherein the biometric data indicates a pulse of the user, wherein an increase in the pulse of the user above an upper predetermined pulse level increases the level of distress or a decrease in the pulse of the user below a lower predetermined pulse level increases the level of distress.

* * * * *